United States Patent [19]

Norris

[11] Patent Number: 4,957,686

[45] Date of Patent: Sep. 18, 1990

[54] USE OF BACTERIOPHAGES TO INHIBIT DENTAL CARIES

[76] Inventor: Alan H. Norris, 120 Saddle Mountain Rd., Rome, Ga. 30161

[21] Appl. No.: 473,888

[22] Filed: Feb. 6, 1990

[51] Int. Cl.$^5$ .......................... A61K 7/16; A61K 9/68; A61K 39/02

[52] U.S. Cl. ........................................ 424/50; 424/48; 424/49; 424/92; 424/480; 424/441; 426/3; 132/321

[58] Field of Search .................. 424/48, 49, 50, 92, 424/440, 441

[56] References Cited

U.S. PATENT DOCUMENTS

| | | | |
|---|---|---|---|
| 2,944,941 | 7/1960 | Goldenberg | 424/50 |
| 4,150,116 | 4/1979 | Taubman et al. | 424/50 |
| 4,337,314 | 6/1982 | Oeschger et al. | 424/92 |
| 4,631,259 | 12/1986 | Clewell et al. | 435/172.3 |
| 4,659,561 | 4/1987 | Fives-Tylor et al. | 424/50 |
| 4,672,032 | 6/1987 | Slavkin | 424/49 |
| 4,681,762 | 7/1987 | Oeschger et al. | 424/92 |
| 4,681,852 | 7/1987 | Tribe | 435/172.3 |
| 4,891,210 | 1/1990 | Norris | 424/50 |

FOREIGN PATENT DOCUMENTS 727195 4/1980 U.S.S.R.

OTHER PUBLICATIONS

Golub et al. Chem. Abstr. 93:155860z (1980).

*Primary Examiner*—Shep K. Rose

[57] ABSTRACT

Because *S. Sanguis* is the first colonizer of newly cleaned teeth and because other bacteria then attach to it, the formation of dental plaque is reduced on newly cleaned teeth by introducing into the mouth bacteriophages which are parasitic to *S. Sanguis*. Because *S. Sanguis* is the means of attachment of plaque forming bacterial colonies to tooth surfaces and forms 10–15% of the organisms in plaque, destruction of *S. Sanguis* by introduction of its parasitic bacteriophages will remove plaque from teeth surfaces. And removal of plaque containing acid forming bacteria and other harmful bacteria reduces the incidence of dental caries and other disease.

10 Claims, No Drawings

USE OF BACTERIOPHAGES TO INHIBIT DENTAL CARIES

CROSS REFERENCE TO RELATED APPLICATIONS

1. U.S. Pat. No. 4,659,561, Apr. 21, 1987 Entitled "Process for treating the oral cavity". Inventors Paula Fives-Taylor, Charles P. Novotny.
2. U.S. Pat. No. 4,891,210, Jan. 2, 1990 entitled "Use of Bacteriophages in Dental Hygiene". Inventor Alan H. Norris. of which this application is a continuation in part.

BACKGROUND OF THE INVENTION

The most recent conclusions on the causation of dental caries are expressed in U.S. Pat. No. 4,659,561. These envisage that the initial breach in the tooth enamel, which is the tooths protective surface, is made by acid forming bacteria. Once the enamel is damaged, many other bacteria can further attack and erode the dentine. But while the enamel is intact, bacteria other than acid forming bacteria do not cause cavities. There are many types of bacteria which form acid including *Streptococcus mutans*, strains of Lactobacillus and others.

U.S. Pat. No. 4,659,561, teaches that studies of newly cleaned teeth and newly erupted teeth of infants show they are first colonised by bacteria known as *Streptococcus Sanguis*. And it is only after initial attachment of the *S. Sanguis* cells to sites on the salivary pellicle, and their proliferation there, that a secondary colonisation by *S. Mutans* and other bacterial species takes place by attachment of cells thereof to receptor sites on the *S. Sanguis* cells. And further, that if the initial attachment of the *S. Sanguis* organisms can be prevented, the attachment of *S. Mutans*, which is an acid forming bacteria, and other dental caries producing organisms, would be inhibited or substantially reduced. That patent suggests treatments to reduce the attachment of *S. Sanguis* bacteria to the teeth by use of a vaccine to elicit antibodies in the saliva and other means such as fibrial antigens.

U.S. Pat. No. 4,891,210 teaches the use of bacteriophages, which can attack and destroy specific bacteria to reduce or eliminate the acid forming bacteria which initiate dental caries. This treatment would require inserting into the oral cavity, at repeated intervals, a mixture of phages; (bacteriophages will henceforth be abbreviated to phages) such mixture containing phages which are parasitic to most, if not all, acid forming bacteria which can be found in oral cavities. This is a practical method because although the number of types of phages needed may be many, the bacteria and phages for each bacteria are known and can be obtained from commercial companies such as the American Type Culture Collection of Rockville, Maryland. And once the host bacteria and the respective phage have been obtained, propogation of phages in immense numbers is both practical and inexpensive.

SUMMARY OF THE INVENTION

The prior art, as expressed in U.S. Pat. No. 4,659,561, suggests that the chain of causation of dental caries can be broken without destruction of the acid forming bacteria if their attachment to the tooth surface can be inhibited by removal of the *S. Sanguis* bacteria which provide their adherence means. The invention herein comprises two methods. First, that the mixture of phages as indicated in U.S. Pat. No. 4,891,210 should include phages destructive to *S. Sanguis* and other bacteria which can provide initial colonisation of clean tooth surfaces. And second that a mixture of protective phages may need only contain phages destructive of *S. Sanguis* and other bacteria which can provide primary tooth adherence for secondary colonisation by harmful bacteria. This latter method would very much reduce the number of different phages required in the phage preventitive treatment of dental caries.

If only *S. Sanguis* bacteria provided tooth adherence for all other bacteria, then only *S. Sanguis* phages need be provided to eminiate adherence of all bacteria. The elimination of *S. Sanguis* bacteria would, in addition to reducing dental caries, also reduce the plaque development on the teeth, since the development of plaque is disrupted if adherence of a first coloniser *S. Sanguis* is blocked. The bacteria entering the mouth would have much reduced means of adherence to teeth and would be removed from the mouth through the swallowing of saliva. And, further, if the teeth were already coated with phage and *S. Sanguis* phage were introduced into the mouth, the destruction of the *S. Sanguis* cells by the phage would clean the teeth of the colonies of bacteria held in place by the *S. Sanguis* cells since their indirect adhesion to the teeth surface would be destroyed as the *S. Sanguis* cells were destroyed by the phage. Indeed the presence of a plaque film would provide an environment which would absorb and retain the phages and reduce their removal by saliva. And the phage penetration would reach inderdental cavities not easily reached by brushing, if these contained plaque which could absorb the phage. So the presence of some plaque would be of advantage to the phage in that its retention in the mouth would be assured. And exactly in the spaces where it is needed because the presence of plaque implies that this is the location of the *S. Sanguis*.

DESCRIPTION OF THE INVENTION

U.S. Pat. No. 4,659,561, teaches that the surface of the enamel of the teeth is a complex salt of calcium and phosphate called hydroxy apatite. When normal teeth enamel surfaces are cleaned with abrasive down to the enamel surface and then exposed to normal fluids of the oral cavity, a thin film of absorbed salivary components called an "acquired pellicle" forms first on the surfaces. The pellicle is generally less than a micron in thickness and provides the receptor sites for the first microbial colonisers of the teeth. Its components include blood-group-reactive salivary mucins and it is believed by some skilled in the art that these serve as bacterial receptors on the tooth surface. For some, but not all kinds of bacteria.

Dental plaque formation is thought to involve two types of specific bacterial adherent interactions. Bacteria first attach, on a selective basis, to the acquired pellicle. In a second stage bacteria accumulate by means of specific interactions with components of the existing plaque formed by the initially attaching bacteria. It has been found that bacteria known as Streptococcus Sanguis are the first substantial colonisers of freshly cleaned teeth. After an initial attachment of the *S. Sanguis* cells, and their profileration, a secondary colonisation by *S. mutans* and other bacteria takes place by attachment to *S. Sanguis* cells. The *S. Mutans* bacteria and other microorganisms continue to build until the total bacterial layer may be several hundred cells thick. The *S. mutans* and other acid producing bacteria such as Lactobacillae and Actinomyces sp and various anaerobic bacteria can act on starches and sugars to produce as side products of their feeding various organic acids. Inside the plaque film and close to the tooth enamel the acids are not diluted by saliva and can, and do, reach concentrations which demineralise the hydroxy apatite of the tooth enamel by reacting with the calcium therein. This destruction of the protective enamel allows further attack on the meterial of the tooth and, eventually, a cavity is formed. It has been shown in the prior art that if the *S. Sanguis* are not present, then the acid forming bacteria do not easily attach to the acquired pellicle and do not form the heavy layer of plaque needed to allow acid concentration resulting in caries.

From the above it is apparent that if the *S. Sanguis* bacteria are inhibited from establishing colonies on the clean tooth surface that the acid forming bacteria will not be able to attach to the tooth surface, that plaque will not form, and that dental caries will be prevented.

The methods of this invention propose using phages which are parasitic to *S. Sanguis* to destroy the *S. Sanguis* bacteria and thus inhibit the plaque forming process leading to dental caries.

Phages are viruses which are parasitic to bacteria. In very simple terms a phage comprises a cell wall, an interior containing DNA and a tail. Each phage is specific to one kind of bacteria and does not attack other cells, bacterial or other. When the phage contacts the bacteria, the tail pierces the bacterial cell well and then acts as a conduit through which the phage DNA enters the bacterial cell. There, the DNA reorders the bacterial proteins to produce new phages. In approximately 30-60 minutes the bacterial cell wall bursts to release a multiplicity of new phages into the environment. These phages then contact other bacteria of the kind to which they are specific and destroy these, creating in the process an ever larger number of phages until the supply of bacteria on which to act runs out. Bacteriophages are well known and completely described in the prior art. In an earlier specification resulting in U.S. Pat. No. 4,891,210 the method of using active phages in the mouth to reduce the number of acid forming bacteria was described.

This invention relates to a method of preventing dental caries by using phages parasitic to the *S. Sanguis* bacteria, either alone or in conjunction with a mixture of phages containing such variety as to contain phages which attack *S. Mutans*, Lactobaccilii and any other bacteria which may cause caries or gum disease, to reduce the receptor sites of *S. Sanguis* on the tooth surface for such acid forming bacterial colonisation.

The phages may be introduced into the mouth by tablet or liquid or spray, or may be contained in food or drink, or may be in toothpaste, dental floss or tooth cleaning powder, or other means. The phages should be introduced at intervals of not more than 2 days, the formation of a thick plaque layer taking 2-3 days. It may be advantageous to introduce the phages at night after tooth cleaning so that there is a minimum loss of phages by saliva action. Peoples secretion of saliva when sleeping is minimal. But it is highly probable that some of the phages would be absorbed into the surface of any plaque present in the mouth. Once deposited on and in the plaque the phages would find and destroy the bacteria to which they were parasitic. If only phages parasitic to *S. Sanguis* were used, the other bacteria would be unharmed. However, as the *S. Sanguis* bacteria were destroyed, the attachment of the plaque film to the teeth would be much weakened and they would no longer adhere to the tooth surfaces. As they are released from the tooth surface the acid forming bacteria can no longer produce a high acid concentration in proximity to the tooth enamel and dental caries would be inhibited.

The prior art indicates that bacteria are associated with diseases of the mouth other than dental caries. It is believed that periodontosis is caused by the presence of a bacteria named actinobacillus actinomycetemcomitans. It is believed that gingival inflammation is caused by a bacteria named staphylococcus aureus and other bacteria. The methods of the invention may be used to reduce the incidence of these diseases. In practice these diseases are only treated after symptoms of the disease are very apparent. Prevention is far better than cure.

Using the methods of the invention by regularly placing in the mouth phages parasitic to *S. Sanguis* and thus preventing the build up of plaque, there is no way that concentrations of other bacteria can be formed which concentrations over time would have led to periodontoses, gingivitis and pyorrhea. Thus the methods of the invention are protective of these dental diseases as well as dental caries. The methods of this invention are primarily to destroy by bacteriophages those bacteria which are not harmful themselves but which facilitate colonisation of tooth surfaces by providing receptor sites to which harmful bacteria can adhere.

What I claim is:

1. A method of improved dental hygiene comprising introducing into the mouth bacteriophages parasitic to bacteria which possess the property of readily adhering to the salivary pellicle, said bacteria so providing receptor sites for other bacteria and so allowing a build up of plaque on the teeth.

2. Claim 1, in which the said bacteria are *S. Sanguis*.

3. A method of improved dental hygiene comprising introducing into the mouth a mixture of bacteriophages parasitic to bacteria normally present in the mouth, said mixture of bacteriophages containing at least one bacteriophage parasitic to *S. Sanguis*.

4. Claim 1, wherein the bacteriophages are incorporated in toothpaste.

5. Claim 1, wherein the bacteriophages are incorporated in toothpowder.

6. Claim 1, wherein the bacteriophages are incorporated in dental floss.

7. Claim 1, wherein the bacteriophages are incorporated in chewing gum.

8. Claim 1, wherein the bacteriophages are incorporated in oral tablets.

9. Claim 1, wherein the bacteriophages are incorporated in mouthwash solutions.

10. Claim 1, wherein the bacteriophages are incorporated in sweets and candy.

* * * * *